United States Patent
Sakanoue et al.

(10) Patent No.: US 10,624,535 B2
(45) Date of Patent: Apr. 21, 2020

(54) ENDOSCOPE APPARATUS AND VIDEO PROCESSOR

(71) Applicant: OLYMPUS CORPORATION, Tokyo (JP)

(72) Inventors: Yoichiro Sakanoue, Hachioji (JP); Yusuke Yabe, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/922,340

(22) Filed: Mar. 15, 2018

(65) Prior Publication Data

US 2018/0199805 A1 Jul. 19, 2018

Related U.S. Application Data

(63) Continuation of application No. PCT/JP2016/053220, filed on Feb. 3, 2016.

(30) Foreign Application Priority Data

Sep. 16, 2015 (JP) .................................. 2015-183168

(51) Int. Cl.
*A61B 1/06* (2006.01)
*A61B 1/04* (2006.01)
(Continued)

(52) U.S. Cl.
CPC ........ *A61B 1/0676* (2013.01); *A61B 1/00009* (2013.01); *A61B 1/04* (2013.01);
(Continued)

(58) Field of Classification Search
None
See application file for complete search history.

(56) References Cited

U.S. PATENT DOCUMENTS

| 10,194,789 B2 | 2/2019 | Seto |
| 2014/0171738 A1 | 6/2014 | Kagaya et al. |
| 2014/0203170 A1* | 7/2014 | Ono ........................ G02B 26/02 250/208.1 |

FOREIGN PATENT DOCUMENTS

| CN | 104135908 A | 11/2014 |
| EP | 2742850 A2 | 6/2014 |

(Continued)

OTHER PUBLICATIONS

International Search Report dated Mar. 8, 2016 issued in PCT/JP2016/053220.

*Primary Examiner* — Clifford Hilaire
(74) *Attorney, Agent, or Firm* — Scully, Scott, Murphy & Presser, P.C.

(57) ABSTRACT

An endoscope apparatus includes: a light-emitting element; a rolling shutter-type image pickup device allowing an exposure period in which the plurality of lines are simultaneously exposed and a reading period in which image pickup signals of the respective lines are sequentially read to be alternately switched to each other; and a control section. The control section controls an intensity of the light emitted by the light-emitting element. The control section can perform switching between a first illumination mode in which the light is applied from the light-emitting element in the exposure period and the reading period and a second illumination mode in which the light is applied from the light-emitting element only in the exposure period, and if the intensity of the light is controlled so as to have a predetermined value, performs control to switch one of the first mode and the second mode to the other.

4 Claims, 4 Drawing Sheets

(51) Int. Cl.
*A61B 1/00* (2006.01)
*A61B 1/045* (2006.01)
*H04N 5/353* (2011.01)
*H04N 5/232* (2006.01)
*H04N 5/235* (2006.01)
*G02B 26/02* (2006.01)
*H04N 5/225* (2006.01)

(52) U.S. Cl.
CPC ............... *A61B 1/045* (2013.01); *A61B 1/06* (2013.01); *G02B 26/02* (2013.01); *H04N 5/2256* (2013.01); *H04N 5/2351* (2013.01); *H04N 5/2353* (2013.01); *H04N 5/2354* (2013.01); *H04N 5/23245* (2013.01); *H04N 5/3532* (2013.01); *A61B 1/0005* (2013.01); *A61B 1/00006* (2013.01); *H04N 2005/2255* (2013.01)

(56) References Cited

FOREIGN PATENT DOCUMENTS

| | | |
|---|---|---|
| JP | 5452785 B1 | 3/2014 |
| JP | 2015061090 A | 3/2015 |
| JP | 5735478 B2 | 6/2015 |
| WO | 2013175908 A1 | 11/2013 |

* cited by examiner

ENDOSCOPE APPARATUS AND VIDEO PROCESSOR

CROSS REFERENCE TO RELATED APPLICATION

This application is a continuation application of PCT/JP2016/053220 filed on Feb. 3, 2016 and claims benefit of Japanese Application No. 2015-183168 filed in Japan on Sep. 16, 2015, the entire contents of which are incorporated herein by this reference.

BACKGROUND OF THE INVENTION

1. Field of the Invention

The present invention relates to an endoscope apparatus and a video processor.

2. Description of Related Art

Conventionally, endoscope apparatuses have widely been used in a medical field and an industrial field. An endoscope apparatus generates an endoscopic image, which is an image of a subject, as a result of an insertion portion being inserted to the inside of the subject, illuminating light being applied to a site to be examined and reflected light from the site to be examined being received by an image pickup device.

In recent years, endoscope apparatuses each using a CMOS image sensor as an image pickup device have been provided. CMOS image sensors employ a rolling shutter method in which exposure and reading are performed with a timing shifted for each line, and processing from exposure to reading is performed at a timing that is different for each line.

In the case of CMOS image sensors, when pulsed illumination is provided, exposure unevenness may occur depending on the timing of emission of the illuminating light, and thus, as disclosed in Japanese Patent No. 5452785, a technique in which an intensity of illuminating light is kept constant in a video reading timing, that is, a video reading period, and pulsed illumination according to PWM (pulse width modulation) control is performed in an all-line simultaneous exposure timing, that is, an all-line simultaneous exposure period, other than the video reading period, has been proposed. According to the proposal, illumination control that is a combination of PWM control in an all-line simultaneous exposure period and intensity-constant control in a video reading period eliminates exposure unevenness and prevents image quality deterioration.

Also, in the case of illumination control that is a combination of two types of control such as the above proposal, in order to further decrease an illuminating light amount, a method in which a control state in which intensity-constant control is performed in a video reading period and PWM control is performed in an all-line simultaneous exposure period is made to transition to a control state in which current level control and PWM control are performed only in an all-line simultaneous exposure period by stopping the intensity-constant control in the video reading period has been proposed (see FIG. 15).

Then, in order to make the illuminating light amount continuously change before and after the transition, current level control for an all-line simultaneous exposure period after the transition is performed so that the light amount in a video reading period before the transition and the light amount in an all-line simultaneous exposure period after the transition become the same.

SUMMARY OF THE INVENTION

An endoscope apparatus according to an aspect of the present invention is an endoscope apparatus including: a light-emitting section configured to emit light for illuminating a subject; a drive section configured to generate a drive signal for causing the light to be emitted from the light-emitting section, the drive section enabling an amount of the light emitted by the light-emitting section to be changed according to a current value of the drive signal; a rolling shutter-type image pickup device including a plurality of lines that receive reflected light from the subject to which the light is applied, the image pickup device being configured to allow an exposure period in which the plurality of lines are exposed and a reading period in which image pickup signals of the respective lines are sequentially read from the plurality of lines to be alternately switched to each other; and a control section configured to generate an endoscopic image from the image pickup signals generated by the image pickup device and perform control of switching between a first mode for controlling the drive section so that the light is applied from the light-emitting section in the exposure period and the reading period and a second mode for controlling the drive section so that the light is applied from the light-emitting section only in the exposure period, the control section being configured to, if the current value of the drive signal is a predetermined lower limit value in the first mode and a brightness of the endoscopic image is further lowered, perform switching from the first mode to the second mode, wherein the control section controls the drive section so that the image pickup device performs simultaneous exposure of the plurality of lines in the entire exposure period and controls the drive section so that a light amount in the exposure period in a field or a frame immediately after the switching from the first mode to the second mode is a light amount obtained by adding a part of a light amount in the reading period in a field or a frame immediately before the switching from the first mode to the second mode to a light amount in the exposure period in the field or the frame immediately before the switching from the first mode to the second mode.

A video processor according to an aspect of the present invention is a video processor for, upon an input of an image pickup signal from a rolling shutter-type image pickup device including a plurality of lines that receive reflected light from a subject to which light for illuminating the subject is applied from a light-emitting section configured to emit the light, the image pickup device being configured to allow an exposure period in which the plurality of lines are exposed and a reading period in which image pickup signals of the respective lines are sequentially read from the plurality of lines to be alternately switched to each other, generating an endoscopic image, the video processor including a control section configured to perform control of switching between a first mode for controlling a drive section that enables an amount of the light emitted by the light-emitting section to be changed according to a current value of a drive signal so that the light is applied from the light-emitting section in the exposure period and the reading period, and a second mode for controlling the drive section so that the light is applied from the light-emitting section only in the exposure period, the control section being configured to, if the current value of the drive signal in the first mode is a predetermined lower limit value and a brightness of the endoscopic image is further lowered, perform switching from the first mode to the second mode, wherein the control section controls the drive section so that the image pickup device performs simultaneous exposure of the plurality of lines in the entire exposure period and controls the drive section so that a light amount in the exposure period in a field or a frame immediately after the switching from the first mode to the second mode is a light amount obtained by adding a part of a light amount in the reading period in a field or a frame immediately before the switching from the first mode to the second mode to a light amount in the exposure period in the field or the frame immediately before the switching from the first mode to the second mode.

DETAILED DESCRIPTION OF PREFERRED EMBODIMENT

An embodiment will be described with reference to the drawings.

Figure 1:
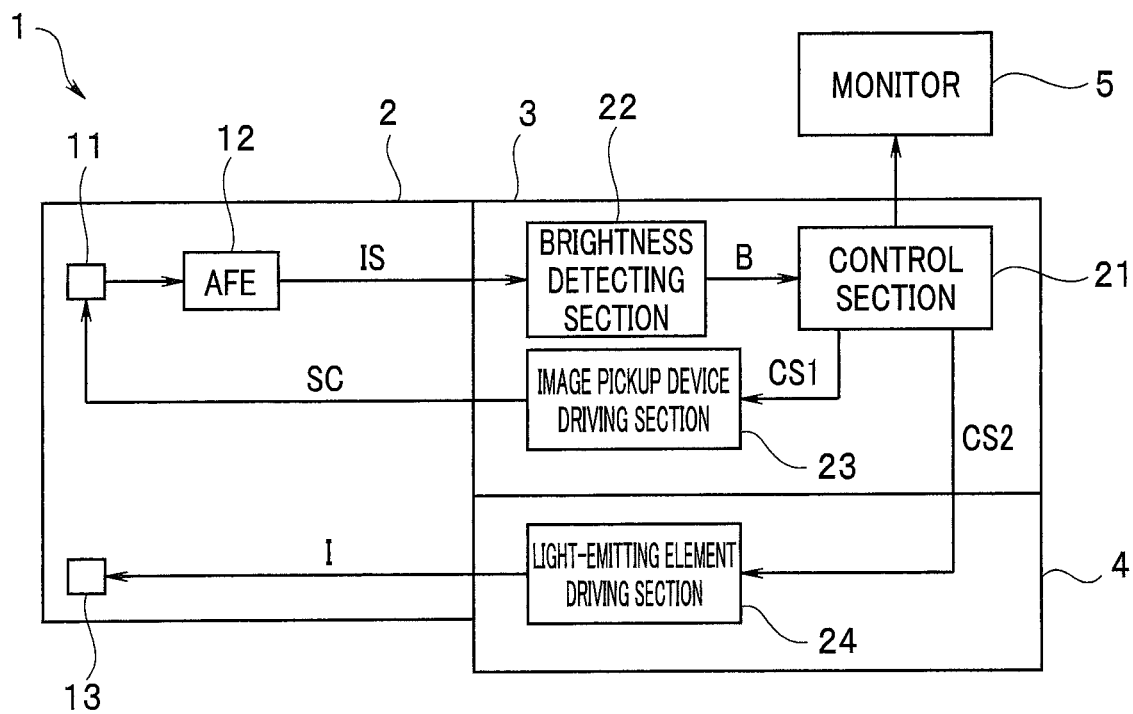
FIG. 1 is a block diagram illustrating a configuration of an endoscope apparatus according to an embodiment of the present invention.

FIG. 1 is a block diagram illustrating a configuration of an endoscope apparatus according to the present embodiment. The endoscope apparatus 1 includes an endoscope 2, a video processor 3, a light source apparatus 4 and a monitor 5. Note that, in FIG. 1, only components related to illumination timing change in the present embodiment are illustrated and illustration of the other components is omitted.

The endoscope 2 includes an image pickup device 11, an analog front-end section (hereinafter referred to as AFE section) 12 and a light-emitting element 13.

The image pickup device 11 is a CMOS image sensor, and upon being driven by a later-described image pickup device driving section 23, outputs an image pickup signal to the AFE section 12. The image pickup device 11 includes a light receiving section including a plurality of horizontal lines each including a plurality of pixels. The image pickup device 11 generates an image according to a rolling shutter method in which exposure and reading are performed with a timing shifted for each of the horizontal lines.

The AFE section 12 subjects an image pickup signal, which is an inputted analog signal, to, e.g., noise reduction processing and amplification processing and then converts the resulting signal to a digital signal and outputs the digital signal to the video processor 3.

The light-emitting element 13 is, for example, a light-emitting diode (LED) configured to emit white light, and is a light-emitting section configured to, upon being driven by a later-described light-emitting element driving section 24, emit illuminating light for illuminating a subject.

The image pickup device 11 and the light-emitting element 13 are disposed in a distal end portion of an insertion portion of the endoscope 2.

The video processor 3 includes a control section 21, a brightness detecting section 22 and the image pickup device driving section 23.

The control section 21 includes, e.g., a central processing unit (CPU), a ROM and a RAM, and performs control of the entire endoscope apparatus 1 and control of respective sections. More specifically, the control section 21 performs control of driving of the image pickup device 11 and the light-emitting element 13 and various image processing on an image pickup signal from the image pickup device 11 to, e.g., generate an image to be displayed on the monitor 5 and to record the image in a non-illustrated memory.

The brightness detecting section 22 is a circuit configured to, based on an image pickup signal IS from the image pickup device 11 in the endoscope 2, calculate a brightness of an image, from pixel values of a plurality of pixels included in a predetermined range, for example, an entire frame image range.

The image pickup device driving section 23 is a circuit configured to generate a drive signal SC based on an image pickup device control signal CS1 from the control section 21 to drive the image pickup device 11. The drive signal SC contains a synchronization signal that provides an exposure timing and a reading timing to the image pickup device 11.

The light source apparatus 4 includes a light-emitting element driving section 24.

As described later, the control section 21 outputs a light-emitting element driving control signal CS2 at a predetermined timing.

The light-emitting element driving section 24 is a circuit configured to, based on a light-emitting element driving control signal CS2 from the control section 21, generate a drive signal I, which is a current signal, to drive the light-emitting element 13. An intensity of light emitted by the light-emitting element 13 varies according to a magnitude, that is, a current value of the drive signal I outputted from the light-emitting element driving section 24.

The control section 21 controls switching between two illumination modes, which will be described later, and in each illumination mode, controls an intensity of illuminating light emitted by the light-emitting element 13 so that a brightness of an image becomes a proper brightness, based on a brightness signal B detected by the brightness detecting section 22. In other words, the control section 21 configures a light-emitting control section configured to control an intensity of light emitted by the light-emitting element 13, which is a light-emitting section.

Illuminating light from the light-emitting element 13 provided in the distal end portion of the insertion portion of the endoscope 2 illuminates a site to be observed in a subject, reflected light of the illuminating light is received by the image pickup device 11 and an image pickup signal IS is generated.

The monitor 5 is a display apparatus, such as a liquid-crystal display, configured to display an endoscopic image and a menu image.

As described above, the brightness detecting section 22 detects a brightness of an image of each frame based on an image pickup signal IS from the AFE, section 12 and outputs a brightness signal B indicating the brightness of the image of each frame to the control section 21. The control section 21 generates a display image based on the received image pickup signal IS, and based on the received brightness signal B, outputs a light-emitting element driving control signal CS2 to the light-emitting element driving section 24.

Therefore, the control section 21 controls the image pickup device driving section 23 to drive the image pickup device 11, generates an endoscopic image from image data generated according to the rolling shutter method and outputs the endoscopic image to the monitor 5 to display the endoscopic image.

Figure 2:
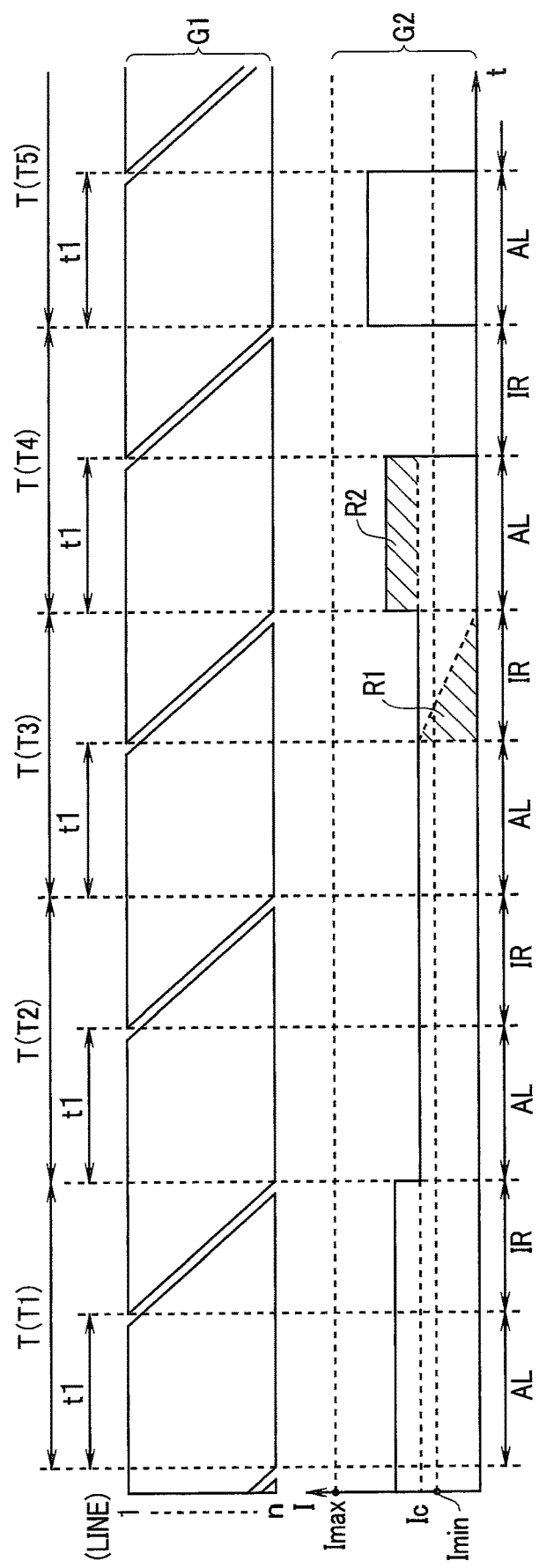
FIG. 2 is a schematic diagram for describing a relationship between an exposure period and a reading period in an image pickup device 11 during image pickup in an endoscope apparatus 1 and an output of illuminating light emitted by a light-emitting element 13, according to the embodiment of the present invention.

FIG. 2 is a schematic diagram for describing a relationship between an exposure period and a reading period in the image pickup device 11 during image pickup in the endoscope apparatus 1, and an output of illuminating light emitted by the light-emitting element 13.

In FIG. 2, timings of an exposure period and a reading period for each line in the image pickup device 11 are schematically illustrated in the range indicated by G1 in the upper part. G2 in the lower part indicates variation of a drive signal I flowing in the light-emitting element 13. The horizontal axis represents a time t.

The image pickup device 11 is a CMOS image sensor, and the image pickup device 11 includes a light receiving section including n rows of lines each including a plurality of pixels. The image pickup device 11 generates image data according to the rolling shutter method in which exposure and reading are performed with a timing shifted for each line.

More specifically, when the image pickup device 11 successively picks up images of a plurality of frames, the image pickup device 11 performs reading of accumulated charge for each horizontal line. Lines from a first line (first-row line in FIG. 2) to an n-th line (n is a natural number and the n-th line is the n-th row line in FIG. 2), which is a last line, in the light receiving section of the image pickup device 11 are sequentially read and pixel signals are thus read. Therefore, a time difference occurs in reading timing between the first-row line and the n-th row line.

A period of time from a start of reading of pixel data from the first line in the image pickup device 11 until an end of reading of pixel data from the n-th line is a video reading period IR.

A period that periodically comes, other than a video reading period IR, in which all the lines are simultaneously exposed is an all-line simultaneous exposure period AL. As illustrated in FIG. 2, a period T for one field or one frame of an image includes an all-line simultaneous exposure period AL and a video reading period IR.

Since the image pickup device 11 is of the rolling shutter type, an all-line simultaneous exposure period AL and a video reading period IR are alternately switched to each other.

A period T for one field (or one frame) and a time period t1 of an all-line simultaneous exposure period AL are determined according to specifications of the image pickup device 11.

As described above, the image pickup device 11 provided in the insertion portion of the endoscope is a rolling shutter-type image pickup device including a plurality of lines that receive reflected light from a subject to which light is applied, the image pickup device 11 allowing an exposure period AL in which a plurality of lines are simultaneously exposed and a reading period IR in which image pickup signals of the respective lines are sequentially read from the plurality of lines to be alternately switched to each other.

A drive signal I outputted by the light-emitting element driving section 24 varies between a predetermined minimum value Imin and a predetermined maximum value Imax. The control section 21 outputs a light-emitting element driving control signal CS2 to the light-emitting element driving section 24. In other words, the light-emitting element driving control signal CS2 is a signal that causes the drive signal I outputted by the light-emitting element driving section 24 to fall between the predetermined minimum value Imin and the predetermined maximum value Imax.

Upon insertion of the insertion portion of the endoscope 2 to the inside of a subject and pickup of an image of the inside of the subject by the image pickup device 11, the control section 21 outputs a light-emitting element driving control signal CS2 that causes the light-emitting element 13 to emit illuminating light having an intensity that allows the image to have a proper brightness, to the light-emitting element driving section 24 according to a brightness of the image detected by the brightness detecting section 22. As a result, an endoscopic image having the proper brightness is displayed on the monitor 5. In other words, the control section 21 performs current level control in which a magnitude of the drive signal I flowing in the light-emitting element 13 is adjusted to perform light control. The current level control is, for example, PAM (pulse amplitude modulation) control.

In FIG. 2, the magnitude of the current value of the drive signal I flowing in the light-emitting element 13 is smaller in period T2 than in period T1. For example, as a result of the distal end of the insertion portion being brought close to the subject, the brightness signal B becomes large, causing a need to decrease an intensity of the illuminating light, and thus, in period T2, the current value of the drive signal I for driving the light-emitting element 13 is lowered.

In each of periods T1 and T2, illumination control is performed in a first illumination mode M1 in which illuminating light having a constant intensity according to a brightness of an image is emitted in an all-line simultaneous exposure period AL and a video reading period IR. As described above, in the first illumination mode M1, the drive signal I is adjusted between the predetermined minimum value Imin and the predetermined maximum value Imax; however, if the distal end portion of the insertion portion of the endoscope 2 is brought too close to the subject, even though the drive signal I has the minimum value Imin, the brightness of the image becomes equal to or exceeds a predetermined brightness.

In other words, the control section 21 normally performs illumination control in the first illumination mode M1 in which illuminating light having a same intensity is emitted in an all-line simultaneous exposure period AL and a video reading period IR in order to obtain an image having a proper brightness.

However, as described above, when the intensity of the illuminating light is too high if the illuminating light is emitted in an all-line simultaneous exposure period AL and a video reading period IR because of the distal end of the insertion portion being brought close to the subject, the control section 21 switches illumination modes so as to perform illumination control in a second illumination mode M2 in which illuminating light is emitted only in an all-line simultaneous exposure period AL in order to obtain an image having a proper brightness.

The second illumination mode M2 is a mode to be executed when a necessary amount of light is small because illuminating light is emitted only in an all-line simultaneous exposure period AL and no illuminating light is emitted in a video reading period IR. In the second illumination mode M2, both current control to increase/decrease the magnitude of the drive signal I to control the intensity of the light and PWM control to control the illuminating light amount according to a time period of light emission are used.

In periods T4 and T5 in FIG. 2, illumination control is performed in the second illumination mode M2 in which illuminating light is emitted only in an all-line simultaneous exposure period AL. In the second illumination mode M2, also, the drive signal I is adjusted between the predetermined minimum value Imin and the predetermined maximum value Imax.

The first illumination mode M1 and the second illumination mode M2 are switched to each other according to a brightness L of a screen.

FIG. 2 indicates that when period T3 transitions to period T4, the illumination control transitions from the first illumination mode M1 to the second illumination mode M2.

(Operation)

Next, operation of the endoscope apparatus 1 will be described.

As described above, the first illumination mode M1 and the second illumination mode M2 are switched to each other according to a brightness L of a screen, and processing for switching between the first illumination mode M1 and the second illumination mode M2 will be described.

Figure 3:
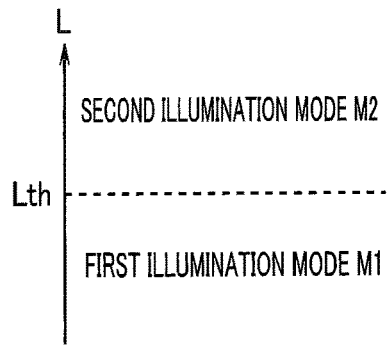
FIG. 3 is a diagram for describing illumination modes according to the embodiment of the present invention.

FIG. 3 is a diagram for describing the illumination modes. The vertical axis in FIG. 3 represents a brightness L. Normally, the control section 21 controls an intensity of illuminating light emitted by the light-emitting element 13 so that a brightness of an image becomes a proper brightness, based on a brightness signal B detected by the brightness detecting section 22. However, when the distal end portion of the endoscope is brought too close to a site to be examined, even if the above-described drive current I has the minimum value Imin, a brightness L of a resulting image does not become a proper brightness and has a value that exceeds a predetermined threshold value Lth.

Therefore, the control section 21 performs illumination control in the second illumination mode M2 if the brightness L of the image calculated based on the brightness signal B from the brightness detecting section 22 exceeds the predetermined threshold value Lth, and performs illumination control in the first illumination mode M1 if the brightness L of the image is equal to or less than the predetermined threshold value Lth. When the brightness L exceeds the predetermined threshold value Lth, and when the brightness L becomes equal to or less than the predetermined threshold value Lth, illumination mode switching is performed.

Figure 4:
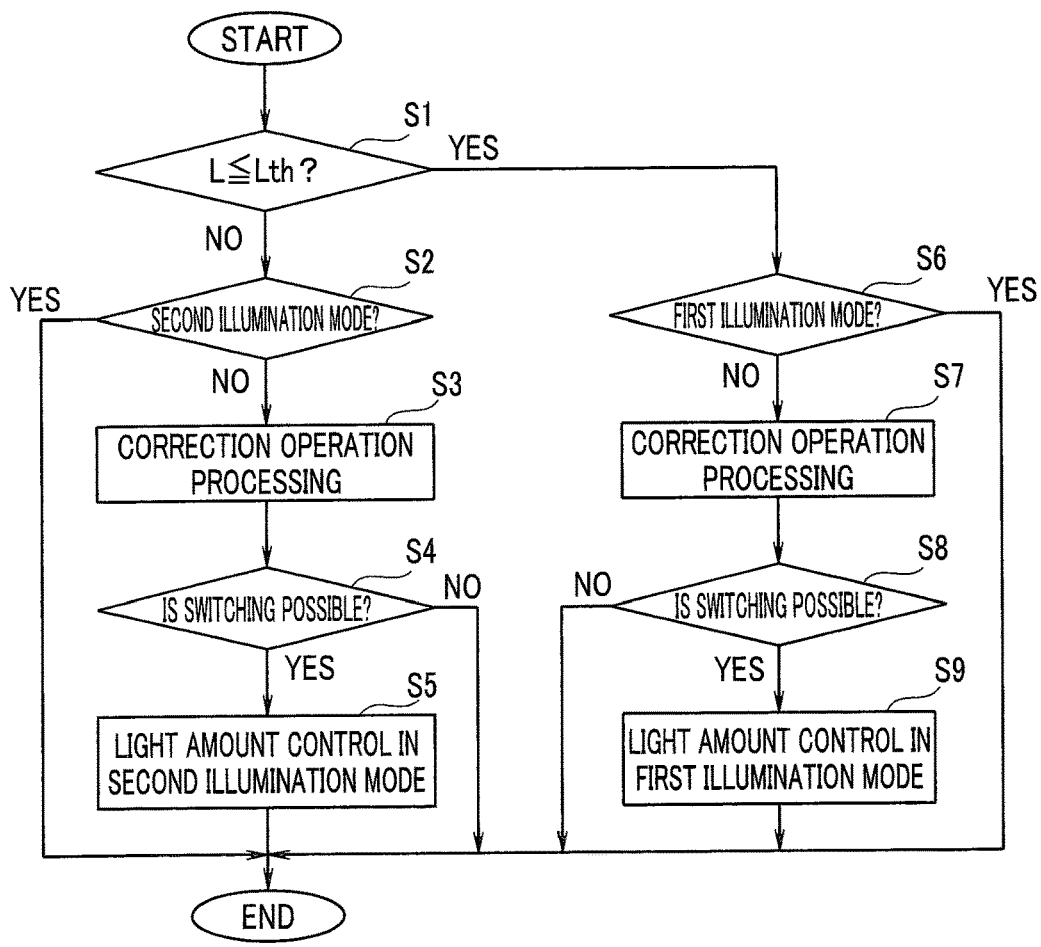
FIG. 4 is a flowchart illustrating an example of a flow of illumination mode switching processing according to the embodiment of the present invention.

FIG. 4 is a flowchart illustrating an example of a flow of illumination mode switching processing. The processing in FIG. 4 is consistently performed when illumination control is performed in the first illumination mode M1 and the second illumination mode M2.

The control section 21 determines whether or not a brightness L of an image is equal to or less than the predetermined threshold value Lth based on a brightness signal B from the brightness detecting section 22 (S1).

If the brightness L of the image is equal to or less than the predetermined threshold value Lth (S1: YES), the control section 21 determines whether or not a current illumination mode is the first illumination mode M1 (S6), and if the current illumination mode is the first illumination mode M1 (S6: YES), the control section 21 does not perform any processing. In FIG. 2, illumination control in the first illumination mode M1 is performed in periods T1 and T2.

If the brightness L of the image exceeds the predetermined threshold value Lth (S1: NO), the control section 21 determines whether or not the current illumination mode is the second illumination mode M2 (S2), and if the current illumination mode is not the second illumination mode M2 (S2: NO), the control section 21 performs correction operation processing (S3).

In FIG. 2, until period T3, the illumination control is performed in the first illumination mode M1, and in period T3, the brightness L of the image exceeds the predetermined threshold value Lth, and in next period T4, the illumination control is performed in the second illumination mode M2.

When the illumination control in the second illumination mode M2 is started from period T4, the correction operation processing (S3) is performed, and a current value in a first field when the illumination control in the second illumination mode M2 is started, here, period T4, is determined.

As illustrated in FIG. 2, where I1 is a current value of a drive signal I in the video reading period IR in the period T3 and I2 is a current value of the drive signal I in the all-line simultaneous exposure period AL in period T4, in order to make a brightness of an image corresponding to an image pickup signal read in the video reading period IR in period T3 and a brightness of an image corresponding to an image pickup signal read in the video reading period IR in period T4 agree to each other, the current value I2 is determined so as to meet equation (1) below:

$$(T-t1)I^{1/2} = t1(I2-I1) \quad (1)$$

The left side of equation (1) indicates the area of shaded region R1 in FIG. 2. The right side of equation (1) indicates the area of shaded region R2 in FIG. 2.

Therefore, in a first field after transition from the first illumination mode M1 to the second illumination mode M2 (period T4 in FIG. 2), an amount of increase in light intensity, in other words, an amount of variation between the current value I1 in period T3 and the current value I2 in period T4 is small, and thus, unevenness in light amount during the transition is less noticeable.

Furthermore, since the current value of the drive signal I in the all-line simultaneous exposure period AL in period T5 after the transition cannot exceed the maximum value Imax, the current values I1 and I2 need to meet expression (2) below.

$$2(I2-I1) + I1 \le Imax \quad (2)$$

Therefore, in the case of NO in S2, the control section 21 performs correction operation processing for calculating a current value I2 meeting the condition in expression (1) above (S3) and determines whether or not illumination mode switching is possible, based on whether or not a result of the correction operation meets the condition in expression (2) above (S4).

Here, as described above, the period T for one field (or one frame) in the image pickup device 11 and the time period t1 of an all-line simultaneous exposure period AL are determined according to the specifications of the image pickup device 11, and thus, the current values I1 and I2 in the respective illumination modes meet expressions (3) and (4) below:

$$Imin \le I1 \le (t1/T)Imax \quad (3)$$

$$I2 \le ((T+t1)/2T)Imax \quad (4)$$

If it is determined that illumination mode switching is possible (S4: YES), the control section 21 performs illumination control in the second illumination mode M2 in which illuminating light is emitted only in an all-line simultaneous exposure period AL, based on a result of the correction operation processing (S5). Here, illumination mode switching is performed.

In S5, the control section 21 performs illumination control for the first field (T4) after the transition from the first illumination mode M1 to the second illumination mode M2 so that a current of the current value I2 determined in S3 is made to flow in the light-emitting element 13. In the subsequent fields (T5 onwards), illumination control is performed in the second illumination mode M2 in which illuminating light is emitted only in an all-line simultaneous exposure period AL, according to the brightness of the image.

As described above, the control section 21 configures a switching control section configured to, when one of two modes that are the first illumination mode M1 in which light from the light-emitting element 13 is applied in an all-line simultaneous exposure period AL, which is an exposure period, and a video reading period IR, which is a reading period, and the second illumination mode M2 in which light from the light-emitting element 13 is applied only in an all-line simultaneous exposure period AL, which is an exposure period is switched to the other, perform control so that an intensity of the light becomes a predetermined value after switching from, here, the first illumination mode M1 to the second illumination mode M2.

Then, the control section 21 controls the intensity of the light emitted by the light-emitting element 13 so that an amount of light received by the image pickup device 11 when the image pickup device 11 is exposed is equal between fields or frames before and after the mode switching. However, in a field or a frame immediately after the mode switching, the control section 21 controls the intensity of the light emitted by the light-emitting element 13 so that a light amount in the exposure period AL in the field or the frame immediately after the mode switching is a light amount obtained by adding a part, here, a half of a light amount in the reading period IR in a field or a frame immediately before the mode switching to a light amount in the exposure period AL in the field or the frame immediately before the mode switching.

More specifically, the control section 21 controls the light-emitting element 13 so that where I1 is an intensity (here, a current value) of the light immediately before the mode switching, I2 is an intensity (here, a current value) of the light immediately after the mode switching, t1 is an exposure period and T is a period for one field or one frame in the image pickup device 11, the relationship in equation (1) is met. Furthermore, the control section 21 controls the light-emitting element 13 so that where Imax is a maximum light emission intensity in the light-emitting element 13, the relationship in expression (2) is met.

If it is not determined that illumination mode switching is possible (S4: NO), the control section 21 does not perform any processing and consequently performs no illumination mode switching.

Here, when the control section 21 determines whether or not the current illumination mode is the second illumination mode M2, if the current illumination mode is the second illumination mode M2 (S2: YES), the control section 21 does not perform any processing and consequently, the illumination control in the second illumination mode M2 is continued.

Also, if the brightness L of the image exceeds the predetermined threshold value Lth (S1: YES), the control section 21 determines whether or not the current illumination mode is the first illumination mode M1 (S6), if the current illumination mode is not the first illumination mode M1 (S6: NO), the control section 21 performs correction operation processing (S7).

In the correction operation processing in S7, the current value I1 of the drive signal I for a first field after the transition from the second illumination mode M2 to the first illumination mode M1 is determined so as to meet equation (1) above.

In other words, in the case of NO in S6, the control section 21 performs correction operation processing for calculating the current value I1 meeting the condition in equation (1) above (S7) and determines whether or not illumination mode switching is possible, based on whether or not a result of the correction operation meets the condition in expression (2) above (S8).

If it is determined that illumination mode switching is possible (S8: YES), the control section 21 performs illumination control in the first illumination mode M1 in which illuminating light is emitted in an all-line simultaneous exposure period AL and a video reading period IR, based on the result of the correction operation processing (S9). Subsequently, the control section 21 performs illumination control in the first illumination mode M1 in which illuminating light is emitted in an all-line simultaneous exposure period AL and a video reading period IR, according to the brightness of the image.

In S9, the control section 21 performs illumination control for the first field after the transition from the second illumination mode M2 to the first illumination mode M1 so that a current of the current value I1 determined in S7 is made to flow in the light-emitting element 13. In the subsequent fields, illumination control is performed in the first illumination mode M1 in which illuminating light is emitted in an all-line simultaneous exposure period AL and a video reading period IR, according to the brightness of the image.

As described above, the control section 21 configures a switching control section configured to perform control so that a light amount becomes a predetermined value after mode switching from the second illumination mode M2 to the first illumination mode M1.

If it is not determined that illumination mode switching is possible (S8: NO), the control section 21 does not perform any processing and consequently, perform no illumination mode switching.

Note that, when the control section 21 determines whether or not the current illumination mode is the first illumination mode M1, if the current illumination mode is the first illumination mode M1 (S6: YES), as described above, the control section 21 does not perform any processing and consequently, the illumination control in the first illumination mode M1 is continued.

As described above, the above embodiment enables provision of an endoscope apparatus and a video processor that reduces luminance unevenness when an illumination timing is changed.

Note that, although in the above embodiment, the light-emitting element 13 emits white light, a plurality of light-emitting elements configured to emit light in a plurality of colors such as RGB may be used, and in such case, a control section performs illuminating light intensity control such as described above at the time of switching of emission of light of the respective colors.

Furthermore, although in the endoscope apparatus according to the embodiment above, the illumination modes are switched to each other based on a brightness of an image, the switching may be performed not based on a brightness of an image. For example, if a current value I1 is a value that prevents a drive signal I from exceeding the predetermined maximum value Imax after switching to the second illumination mode M2, the first illumination mode M1 may be changed to the second illumination mode M2 at an arbitrary timing. Also, if a current value I2 is a value that prevents a drive signal I from falling below the predetermined minimum value Imin after switching to the first illumination mode M1, the second illumination mode M2 may be changed to the first illumination mode M1 at an arbitrary timing. More specifically, if equation (1) and expression (2) above are met in the present example, illumination mode switching may be performed at an arbitrary timing.

Next, modifications of the above embodiment will be described.

(Modification 1)

Although in the above embodiment, a drive signal I is outputted over an entire all-line exposure period in the first illumination mode M1, PWM control may be performed in an all-line exposure period in the first illumination mode M1.

Figure 5:
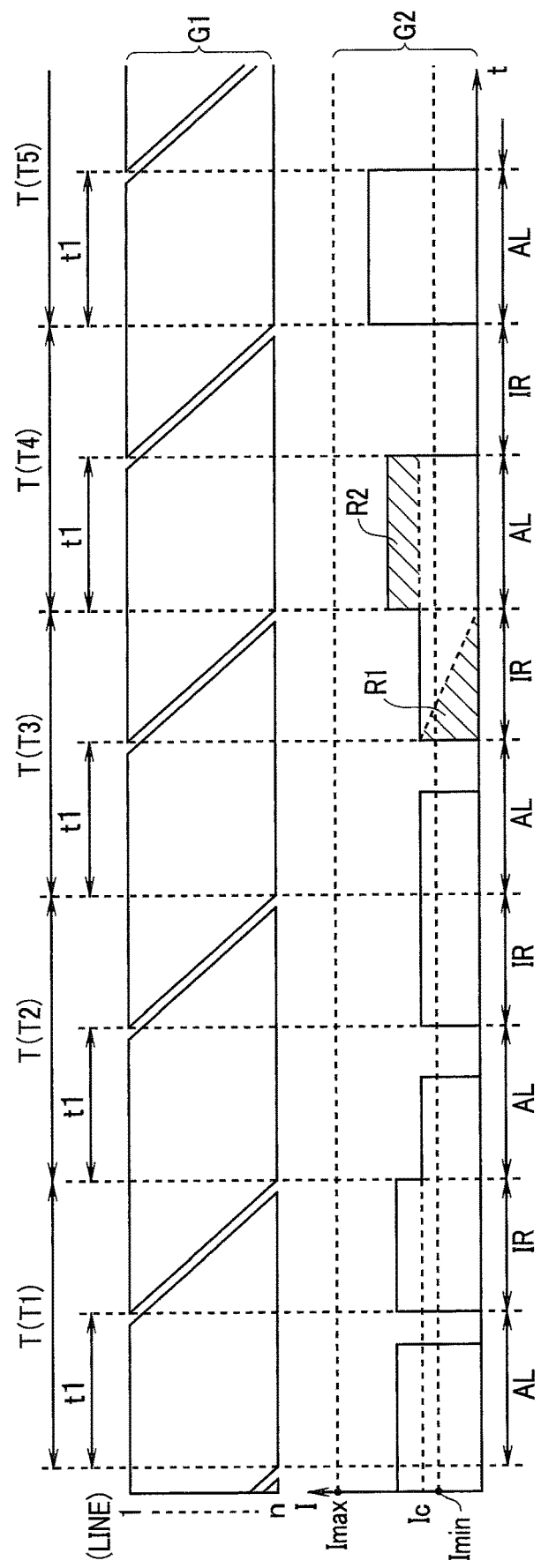
FIG. 5 is a schematic diagram for describing a relationship between an exposure period and a reading period in an image pickup device 11 during image pickup in an endoscope apparatus 1 and an output of illuminating light emitted by a light-emitting element 13, according to modification 1 of the embodiment of the present invention.

FIG. 5 is a schematic diagram for describing a relationship between an exposure period and a reading period in an image pickup device 11 during image pickup in an endoscope apparatus 1 and an output of illuminating light emitted by a light-emitting element 13, according to modification 1. Since FIG. 5 is a diagram that is similar to FIG. 2, description of parts that are in common with FIG. 2 will be omitted.

As illustrated in FIG. 5, in an all-line simultaneous exposure period AL in a period T for one field or one frame of an image, the light-emitting element 13 emits light not over the entire all-line simultaneous exposure period AL, according to PWM control.

As described above, the image pickup device 11 may perform simultaneous exposure of a plurality of lines in a part of an all-line simultaneous exposure period AL, rather than performing simultaneous exposure of the plurality of lines over an entire all-line simultaneous exposure period AL.

In the present modification, also, if a current value I1 is a value that prevents a drive signal I from exceeding a predetermined maximum value Imax after switching to a second illumination mode M2, the first illumination mode M1 may be changed to a second illumination mode M2 at an arbitrary timing. Also, if a current value I2 is a value that prevents a drive signal I from falling below a predetermined minimum value Imin after switching to a first illumination mode M1, the second illumination mode M2 may be changed to the first illumination mode M1 at an arbitrary timing.

If the light-emitting element 13 emits light only in a reading period according to PWM control, a first illumination mode M1 in which light is emitted in a video reading period IR and a second illumination mode M2 in which light is emitted only in an all-line simultaneous exposure period AL may be switched to each other. Also, when one of the first illumination mode M1 and the second illumination mode M2 is switched to the other, as in the above embodiment, a drive signal I may be controlled so that a brightness of an image is equal between before and after mode switching.

(Modification 2)

Since in an image immediately after mode switching, for example, a first field or frame after transition from the first illumination mode M1 to the second illumination mode M2 described above (period T4 in FIG. 2), the image outputted in period T4 has luminance unevenness due to luminance differences among the lines under the influence of illumination in the video reading period IR in period T3, a control section 21 may perform image processing for correcting the image obtained in the first field after transition from a first illumination mode M1 to a second illumination mode M2 (period T4 in FIG. 2) so as to eliminate the luminance unevenness.

In other words, the control section 21 may have a function as a correction section and the correction section may perform processing for correcting luminance unevenness caused under the influence of a light amount in a video reading period IR in a field or a frame immediately before mode switching, for an image in a field or a frame immediately after the mode switching.

As described above, the embodiment and the respective modifications described above each enable provision of an endoscope apparatus and a video processor that reduce luminance unevenness when an illumination timing is changed.

The present invention is not limited to the above-described embodiment, and various changes, alternations and the like are possible without departing from the spirit of the present invention.

What is claimed is:

1. An apparatus, comprising:
   a light source configured to emit light for illuminating a subject;
   a rolling shutter-type image sensor including a plurality of lines that receive reflected light from the subject to which the light is applied, the image sensor being configured to allow an exposure period in which the plurality of lines are exposed and a reading period in which image pickup signals of the respective lines are sequentially read from the plurality of lines to be alternately switched to each other; and
   a control section comprising hardware, the control section being configured to:
      control generation of a drive signal for causing the light to be emitted from the light source, the drive signal enabling an amount of the light emitted by the light source to be changed according to a current value of the drive signal;
      control generation of an endoscopic image from the image pickup signals generated by the image sensor; and
      control switching between a first mode for controlling the light source so that the light is applied from the light source in the exposure period and the reading period and a second mode for controlling the light source so that the light is applied from the light source only in the exposure period, the control section being configured to, if the current value of the drive signal is a predetermined lower limit value in the first mode and a brightness of the endoscopic image is further lowered, control the switching from the first mode to the second mode, wherein the control section, when controlling the switching from the first mode to the second mode if the current value of the drive signal is the predetermined lower limit value in the first mode and the brightness of the endoscopic image is further lowered, controls the image sensor to perform simultaneous exposure of the plurality of lines in the entire exposure period and controls the light source so that a light amount in the exposure period in a field or a frame immediately after the switching from the first mode to the second mode is a light amount obtained by adding a part of a light amount in the reading period in a field or a frame immediately before the switching from the first mode to the second mode to a light amount in the exposure period in the field or the frame immediately before the switching from the first mode to the second mode, and the control section performs control so that where I1 is a light intensity immediately before the switching from the first mode to the second mode, I2 is a light intensity immediately after the switching from the first mode to the second mode, t1 is the exposure period and T is a period for one field or one frame in the image sensor, a relationship in equation (1) below is met $$(T-t1)I1/2 = t1(I2-I1) \qquad (1).$$

2. The endoscope apparatus according to claim 1, wherein the control section further performs control so that where Imax is a maximum light emission intensity in the light source, a relationship in expression (2) below is met:

$$2(I2-I1)+I1 \leq I\text{max} \qquad (2).$$

3. The endoscope apparatus according to claim 1, wherein the control section is further configured to perform processing for correcting luminance unevenness caused under an influence of the light amount in the reading period in the field or the frame immediately before the switching from the first mode to the second mode, for an image of the field or the frame immediately after the switching from the first mode to the second mode.

4. The endoscope apparatus according to claim 1, wherein the image sensor is a CMOS image sensor.

\* \* \* \* \*